United States Patent [19]

Sheppard et al.

[11] Patent Number: 5,268,519

[45] Date of Patent: Dec. 7, 1993

[54] LIGHTLY CROSSLINKED ETHERIMIDE OLIGOMERS

[75] Inventors: Clyde H. Sheppard, Bellevue, Wash.; Hyman R. Lubowitz, Rolling Hills Estates, Calif.

[73] Assignee: The Boeing Company, Seattle, Wash.

[21] Appl. No.: 587,994

[22] Filed: Sep. 25, 1990

Related U.S. Application Data

[62] Division of Ser. No. 213,966, Jul. 1, 1988, Pat. No. 4,981,922, which is a division of Ser. No. 16,703, Feb. 20, 1987, Pat. No. 4,851,495.

[51] Int. Cl.$^5$ .................... C08G 73/10; C08G 8/02; C08G 14/00
[52] U.S. Cl. .................... 578/310; 578/216; 578/125; 578/126; 578/128; 528/170; 528/172; 528/173; 528/185; 528/188; 528/220; 528/229; 528/322; 525/422; 525/426; 525/432; 525/434; 525/436; 428/290; 428/473.5
[58] Field of Search .............. 528/310, 125, 126, 128, 528/170, 172, 173, 26, 185, 188, 322, 220, 229; 428/473.5, 290; 525/432, 434, 422, 426, 436

[56] References Cited

U.S. PATENT DOCUMENTS

| | | | |
|---|---|---|---|
| 3,847,869 | 11/1974 | Williams, III | 528/125 |
| 3,933,862 | 1/1976 | Williams, III | 528/125 |
| 4,058,505 | 11/1977 | D'Alelio | 528/125 |
| 4,075,171 | 2/1978 | D'Alelio | 528/125 |
| 4,107,147 | 8/1978 | Williams, III et al. | 528/172 |
| 4,293,670 | 10/1981 | Robeson et al. | 525/436 |
| 4,297,474 | 10/1981 | Williams, III et al. | 528/170 |
| 4,414,269 | 11/1983 | Lubowitz et al. | 428/290 |
| 4,418,181 | 11/1983 | Monacelli | 525/426 |
| 4,438,280 | 3/1984 | Monacelli | 562/457 |
| 4,476,184 | 10/1984 | Lubowitz et al. | 428/288 |
| 4,504,632 | 3/1985 | Holub et al. | 525/432 |
| 4,536,559 | 8/1985 | Lubowitz et al. | 528/170 |
| 4,547,553 | 10/1985 | Lubowitz et al. | 525/384 |
| 4,556,705 | 12/1985 | McCready | 528/289 |
| 4,584,364 | 4/1986 | Lubowitz et al. | 528/128 |
| 4,604,437 | 8/1986 | Renner | 526/262 |
| 4,611,048 | 9/1986 | Peters | 528/185 |
| 4,657,987 | 4/1987 | Rock et al. | 525/432 |
| 4,661,604 | 4/1987 | Lubowitz et al. | 548/435 |
| 4,663,378 | 5/1987 | Allen | 524/267 |
| 4,684,714 | 8/1987 | Lubowitz et al. | 528/353 |
| 4,695,610 | 9/1987 | Egli et al. | 525/426 |
| 4,727,118 | 2/1988 | Egami | 525/431 |
| 4,769,424 | 9/1988 | Takekoshi et al. | 525/435 |
| 4,835,197 | 5/1989 | Mercer | 524/538 |

FOREIGN PATENT DOCUMENTS 2002378 2/1979 United Kingdom .
81/01855 7/1981 World Int. Prop. O. .

OTHER PUBLICATIONS

K. L. Mittal, (Ed.), Polyimides, vol. 2, pp. 1039-1047.
Kwiatkowski et al., Thermosetting Diphenyl Sulfone-Based Malcimides, Journal Of Polymer Science, vol. 13, pp. 961-972 (1975).

Primary Examiner—John Kight, III
Assistant Examiner—P. Hampton-Hightower
Attorney, Agent, or Firm—Senniger, Powers, Leavitt & Roedel

[57] ABSTRACT

Polyetherimide oligomers having crosslinking end cap moieties which provide improved solvent-resistance to cured composites are generally represented by the formula:

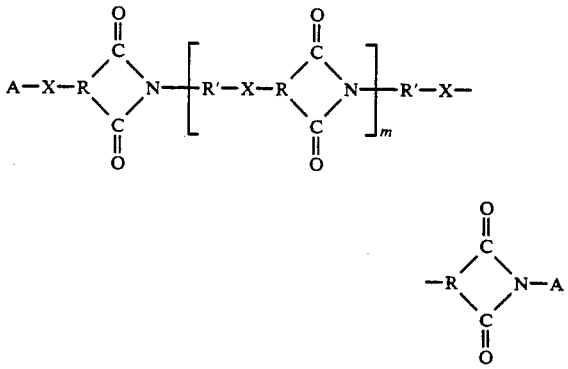

wherein
X=—O— or —S—;

(Abstract continued on next page.)

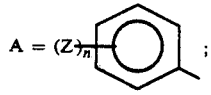

n = 1 or 2;

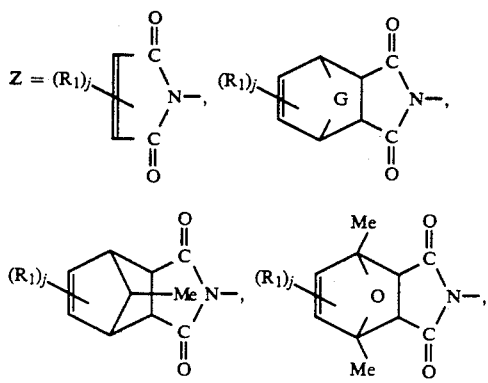

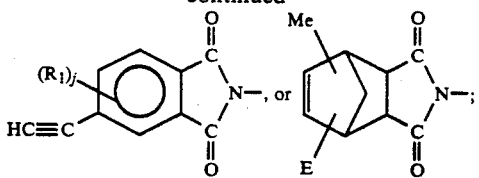

E = allyl or methallyl;
R = a trivalent $C_{(6-13)}$ aromatic organic radical;
$R_1$ = any of lower alkyl, lower alkoxy, aryl, or substituted aryl;
R' = a divalent $C_{(6-30)}$ aromatic organic radical;
j = 0, 1, or 2; and
G = —$CH_2$—, —O—, —S—, or —$SO_2$—

Blends generally comprise substantially equimolar amounts of the oligomers and a comparable, compatible, noncrosslinking, etherimide polymer of substantially the same backbone. The crosslinkable oligomers are made by reacting substituted phthalic anhydrides with hydroxyaryl amines and suitable crosslinking end cap reactants, or by self-condensation of phthalimide salts followed by capping the polymers. Related polyetherimides of the present invention can be prepared by the condensation of nitrophthalic anhydride, diamines, dialcohols (dihydricphenols), and phenolic, crosslinking end caps (A—OH), or the condensation of bis(phenates) or dialcohols (bisphenols), diamines, nitrophthalic anhydride, and amine-terminated end caps (A—$NH_2$) or nitro-terminated end caps (A—$NO_2$).

The oligomers and blends can be prepregged, and can be cured to form advanced composites having aerospace applications.

12 Claims, No Drawings

LIGHTLY CROSSLINKED ETHERIMIDE OLIGOMERS

The present application is a divisional application based upon U.S. patent application Ser. No. 07/213,966, filed Jul. 1, 1988, which now U.S. Pat. No. 4,981,922 is a divisional application based upon U.S. patent application Ser. No. 07/016,703, filed Feb. 20, 1987, now U.S. Pat. No. 4,851,495.

TECHNICAL FIELD

The present invention relates to polyetherimide blended oligomers that are curable into high performance composites and to their method of manufacture. The oligomers have crosslinking end cap functionalities which improve the solvent-resistance of the composites.

BACKGROUND ART

Polyetherimides can be prepared by the self-condensation of hydroxyaryl phthalimide salts, as disclosed in U.S. Pat. No. 4,297,474 (which is incorporated by reference into this description). The polymers have the general formula:

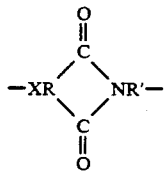

wherein R is a trivalent $C_{(6-13)}$ aromatic organic radical, R' is a divalent $C_{(6-30)}$ aromatic organic radical, and X is —O— or —S—. The polymers have alternating imide and ether (or thioether) linkages between aromatic radicals. Similar polyetherimide polymers are prepared by the reaction of alkali metal dihydric phenol and an organic bis(fluorophthalimide) in the presence of a dipolar aprotic solvent, as disclosed in U.S. Pat. No. 3,847,869 (which also is incorporated by reference into this description). Polysulfoneimides of the same general type are prepared by the reaction of an aromatic bis(sulfoneanhydride) with an organic diamine, as disclosed in U.S. Pat. No. 4,107,147 (which also is incorporated by reference into this description). While these etherimide and sulfoneimide polymers are suitable for films, coatings, etc., their solvent-resistance and other physical properties in composite form can be improved by adding crosslinking end cap functionalities to the polymer backbones, thereby making the composites (cured from the oligomers) better suited for high performance applications, such as aerospace needs.

SUMMARY OF THE INVENTION

Polyetherimide (or sulfoneimides) oligomers of the present invention have the general formula:

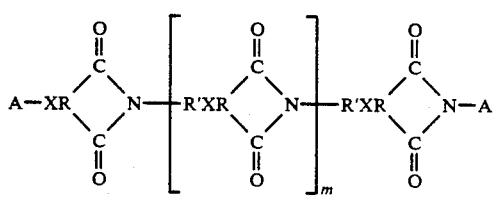

wherein
X = —O— or —S—;

A = 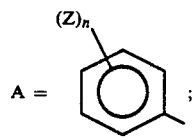

n = 1 or 2;

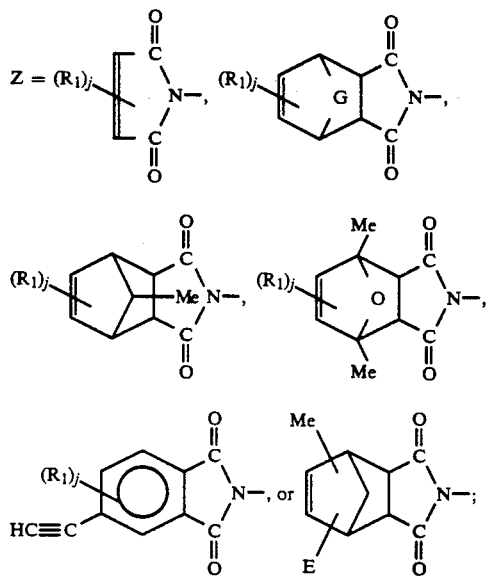

E = allyl or methallyl;
R = a trivalent $C_{(6-13)}$ aromatic organic radical;
$R_1$ = any of lower alkyl, lower alkoxy, aryl, or substituted aryl (including hydroxyl or halo substituents);
R' = a divalent $C_{(6-30)}$ aromatic organic radical;
j = 0, 1, or 2; and
G = —$CH_2$—, —O—, —S—, or —$SO_2$—.

These oligomers can be prepared by condensing:

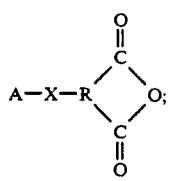  (I)

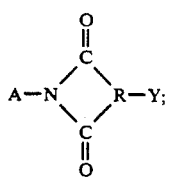  (II)

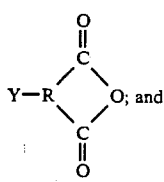  (III)

-continued

 (IV)

in the ratio of I:II:III:IV = 1:1:m:(m+1) wherein m = an integer greater than or equal to one, and A, R, R', and X are as defined previously, and wherein Y = halo- or nitro-. This reaction occurs in a suitable solvent under an inert atmosphere.

Compounds of the formula (I) and (II) are novel compositions of matter. Those of formula (I) can be prepared by reacting A—XH with a substituted phthalic anhydride of the formula:

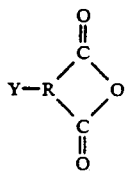 (V)

wherein A, Y, and R are as previously defined. Carried out in a suitable solvent substantially to completion by mixing substantially equimolar amounts of the reactants, the anhydride need not be recovered, but rather the product mixture can be added to the reaction mixture of the condensation reaction of the oligomer, if the solvents are compatible.

Compounds of formula (II) are prepared by reacting A—NH$_2$ with the substituted phthalic anhydride of formula (V). Again, the reaction product need not be separated from the reaction mixture to carry out the oligomer's condensation, if the solvents are compatible.

Blended compositions, preferably having substantially equimolar amounts of the oligomers and a compatible polymer, are also contemplated. These blends generally comprise one of the crosslinkable oligomers previously described and a noncrosslinking polymer of the type described in U.S. Pat. No. 4,297,474 that has substantially the same backbone as the oligomer. Such a polymer, however, does not possess crosslinking capability.

Polysulfoneimide oligomers of the present invention can be prepared by reacting:
n+1 moles of a dianhydride;
n moles of a diamine; and
2 moles of an amine end cap,
wherein the dianhydride and diamine are selected to form a polysulfone imide backbone of the following general formula:

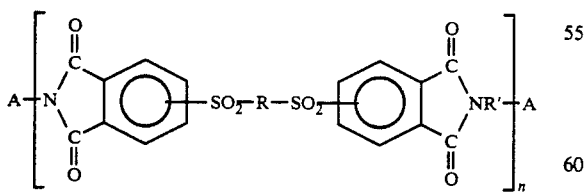

wherein R and R' are divalent aromatic organic radicals having from 2-20 carbon atoms. These radicals include halogenated aromatic C$_{(6-20)}$ hydrocarbon derivatives; alkylene radicals and cycloalkylene radicals having from 2-20 carbon atoms; C$_{(2-8)}$ alkylene terminated polydiorganosiloxanes; and radicals of the formula:

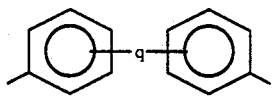

wherein
q = —C$_y$H$_{2y}$—, —CO—, —SO$_2$—, —O—, or —S—; and
y = 1 to 5.

Oligomers of the present invention can also be prepared by the condensation of nitrophthalic anhydride, diamines, dialcohols, and phenolic end caps.

Prepregs and composites of these oligomers and blends can also be made.

BEST MODE CONTEMPLATED FOR CARRYING OUT THE INVENTION

Polyetherimides and polysulfoneimides are capped with mono- and difunctional, crosslinking phenylimides to produce oligomers that are curable to composites which exhibit improved solvent resistance. The end cap phenylimides can be selected to provide cure and use temperatures within a relatively wide range.

Preferred compounds have the general formula:

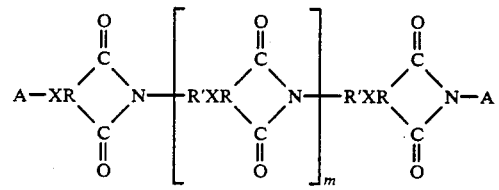

wherein
X = —O— or —S—;

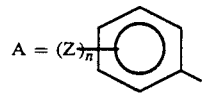

n = 1 or 2;

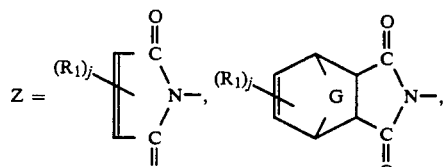

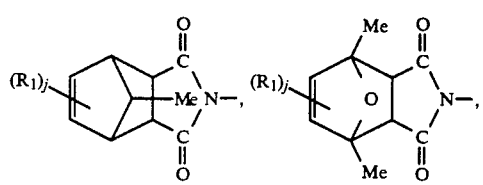

-continued

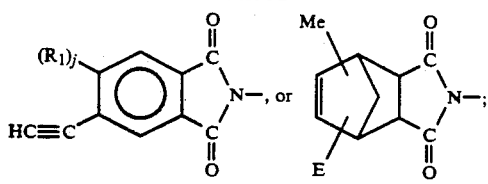 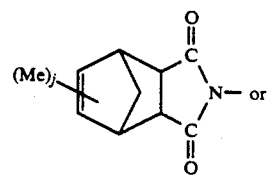

E = allyl or methallyl;
R = a trivalent $C_{(6-13)}$ aromatic organic radical;
$R_1$ = any of lower alkyl, lower alkoxy, aryl, or substituted aryl (including hydroxyl or halo substituents);
R' = a divalent $C_{(6-30)}$ aromatic organic radical;
j = 0, 1, or 2; and
G = —CH$_2$—, —O—, —S—, or —SO$_2$—.

The crosslinking end caps radicals (A) are readily prepared by the condensation of the corresponding anhydride and a suitable amine, as described in U.S. Pat. No. 4,604,437 with respect to the allyl-substituted or methallyl-substituted methylbicyclo[2.2.1]hept-5-ene-2,3-dicarboximides.

The end cap radicals are unsaturated, substituted phenylimides, and are generally selected from the group consisting of:

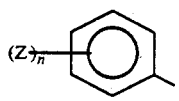

wherein
n = 1 or 2;

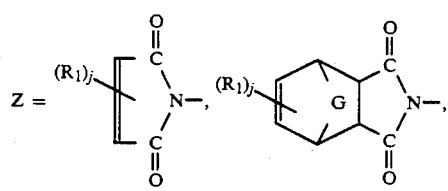

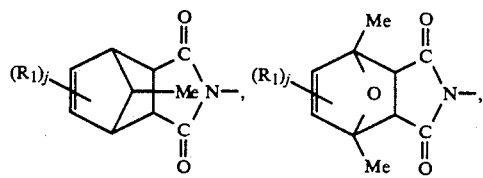

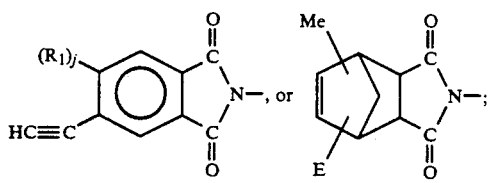

and $R^1$, G, j are as previously defined. The most preferred end caps (to provide the highest thermal stability) are those in which Z has the formulae:

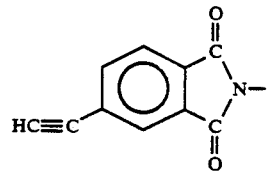

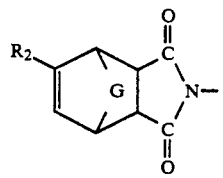

wherein j preferably equals 1. These preferred end caps are conveniently prepared from relatively inexpensive starting materials. Recent work also indicates that an end cap radical of the formula:

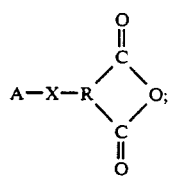

wherein $R_2 =$ 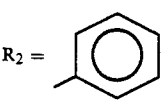

is a preferred compound.

The polyetherimide oligomers of the present invention can be prepared by several reaction schemes. One such method comprises the simultaneous condensation of:

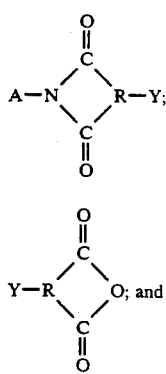

(I)

(II)

(III)

$H_2N$—R'—X—H     (IV)

in the ratio of I:II:III:IV = 1:1:m:(m+1), wherein m is an integer greater than or equal to one. The product has the general formula previously described. The reaction occurs in a suitable solvent under an inert atmosphere. If necessary, the reaction mixture can be heated to facilitate the reaction. The reaction conditions are generally comparable to those described in U.S. Pat. Nos. 3,847,869 and 4,107,147, which are incorporated by reference.

Preferably the oligomer products possess thermoplastic properties, and, accordingly, have an average formula weight of between about 5,000–40,000, and generally 20,000–30,000.

Alternatively, the polyetherimides can be prepared by reacting a polyetherimide polymer made by the self-condensation of a phthalimide salt of the formula:

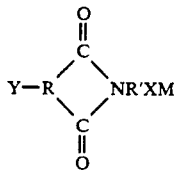

with crosslinking end cap moieties of the formulae:

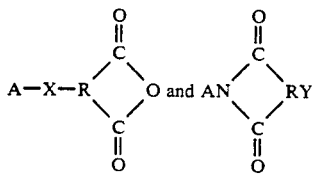

wherein
X = —O— or —S—;

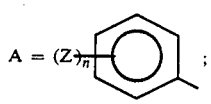

n = 1 or 2;

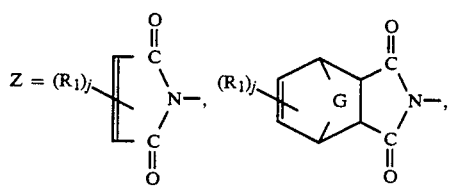

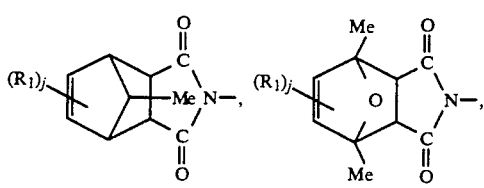

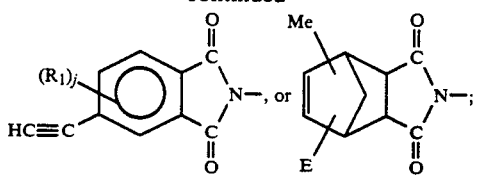

E = allyl or methallyl;
Y = halo- or nitro-;
$R_1$ = any of lower alkyl, lower alkoxy, aryl, or substituted aryl;
R' = a divalent $C_{(6-30)}$ aromatic organic radical;
j = 0, 1, or 2;
G = —CH$_2$—, —O—, —S—, or —SO$_2$—; and
M = an alkali metal ion or ammonium salt or hydrogen.

The self-condensation proceeds as described in U.S. Pat. No. 4,297,474 in a dipolar aprotic solvent. The end cap moieties can be introduced during the self-condensation to quench the polymerization, or they might be added following completion of the polymerization and recovery of the polyetherimide polymer from methanol. Improved solvent resistance on the cured composites is best achieved, however, by the quenching sequence rather than by the post-polymerization capping sequence.

Yet another preferred method for synthesizing the polyetherimides of the present invention involves the simultaneous condensation of about 2m+2 moles of nitrophthalic anhydride with about m+1 moles of diamine, about m moles of dialcohol, and 2 moles of A—OH in a suitable solvent under an inert atmosphere. Here, the dialcohol (hereinafter referred to also as a diol or a dihydric phenol) may actually be in the form of a phenate.

In this reaction, the diamines (which have, preferably, aromatic ethersulfone backbones) react with the anhydride to form intermediates of the following nature in the backbone:

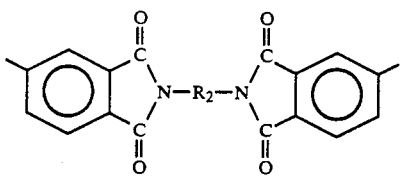

wherein $R_2$ = a residue of the diamine. Similarly, the dialcohol reacts with the nitro-functionality to form an ether linkage of the general formula:

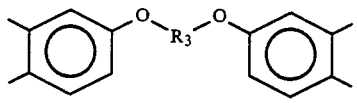

wherein $R_3$ = a residue of the dialcohol.

The A—OH end caps quench the polymerization. The resulting polyetherimides have the general formula:

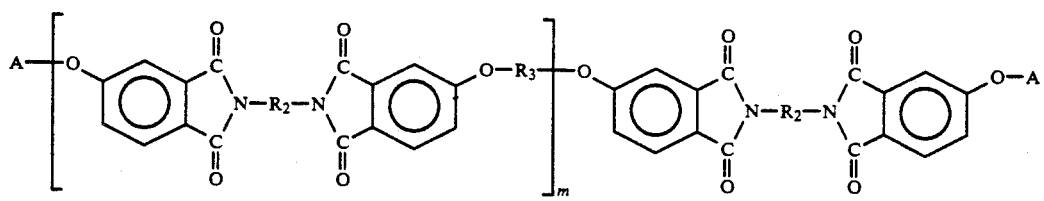

Yet another preferred synthesis comprises the simultaneous condensation of about 2m+2 moles of nitrophthalic anhydride with about m+1 moles of dialcohol, m moles of diamine, and 2 moles A—NH₂ in a suitable solvent under an inert atmosphere. Again, the dialcohol may be in the phenate form. The resulting oligomer has a general formula:

end cap) in a suitable solvent under an inert atmosphere. Again, the dialcohol may be in the phenate form or a corresponding sulfhydryl can be used to form a thiether. The resulting oligomer has the general formula:

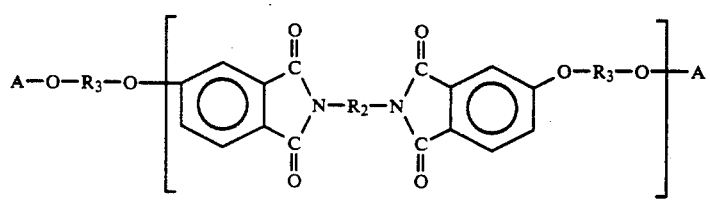

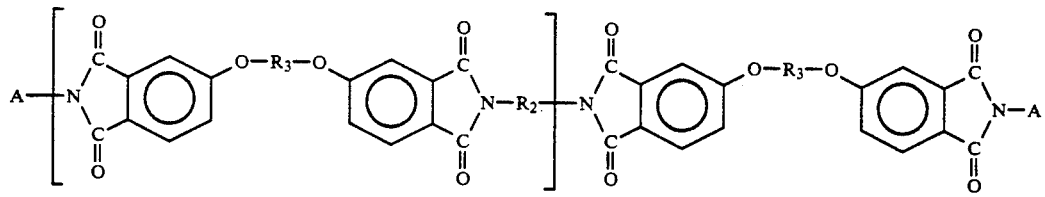

Yet another preferred synthesis comprises the simultaneous condensation of 2m moles of nitrophthalic anhydride with about m+1 moles of dialcohol, m moles of diamine, and 2 moles of A—NO₂ (a nitro-terminated In any of the syntheses, the dialcohol can be replaced by a comparable disulfhydryl of the formula: HS—R₂—SH. Mixtures of dialcohols, or disulfhydryls, or of dialcohols and disulfhydryls can be used.

Suitable diamines are selected from the group consisting of:

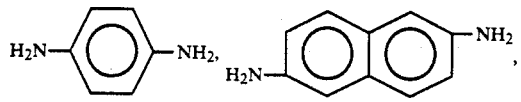

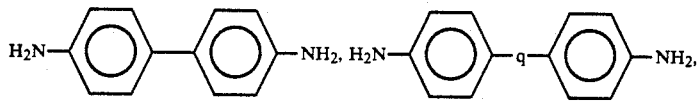

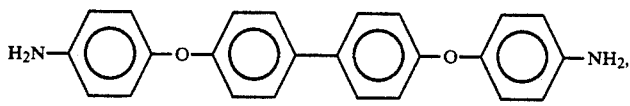

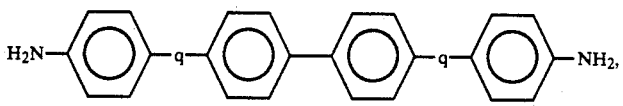

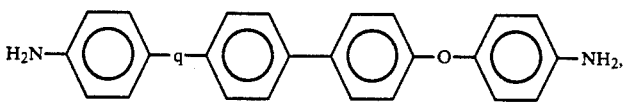

-continued

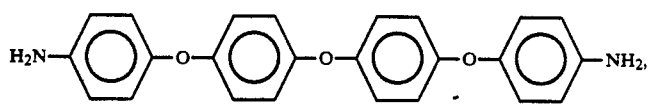

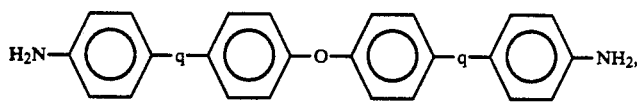

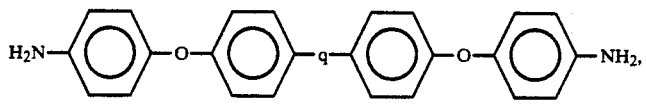

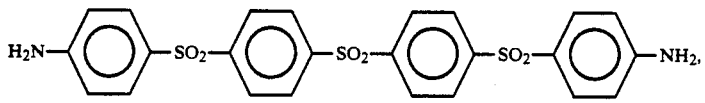

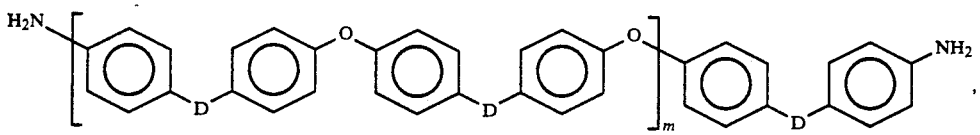

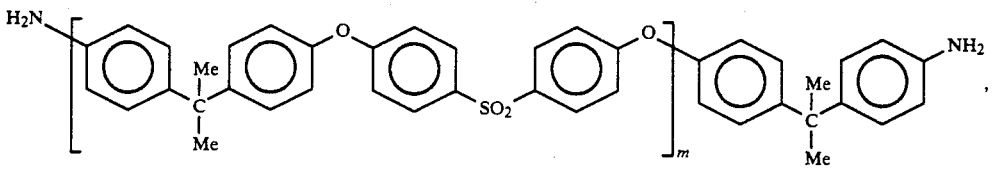

or

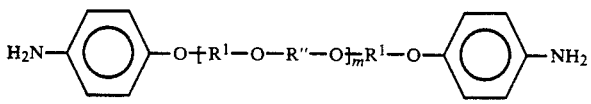

wherein

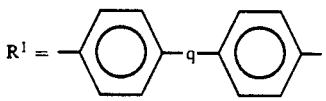

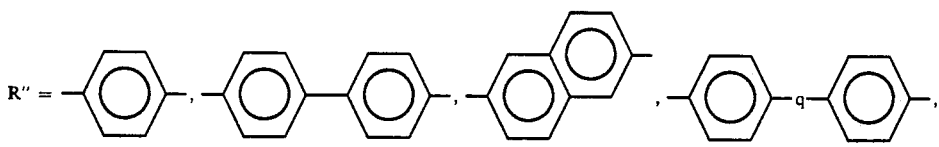

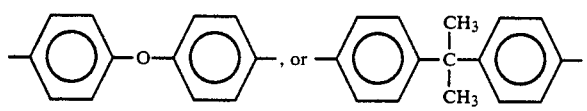

q = —SO$_2$—, —CO—, —S—, or —(CF$_3$)$_2$C—, and preferably —SO$_2$— or —CO—,
Me=CH$_3$—;
m = an integer, generally less than 5, and preferably 0 or 1;
D = any of —CO—, —SO$_2$—, or —(CF$_3$)$_2$C—,; and
X = halogen.

Other diamines that may be used, but that are not preferred, include those described in U.S. Pat. Nos. 4,504,632 and 4,058,505 (which are incorporated by reference). The aryl or polyaryl "sulfone" diamines previously described are preferred, since these diamines provide high thermal stability to the resulting oligomers and composites. Mixtures of diamines might be used.

The dialcohol is generally a polyaryl compound and preferably is selected from the group consisting of:

HO—Ar—OH;

HO—Ar—L—Ar'—L—Ar—OH;

HO—Ar'—L—Ar—L—Ar'—OH;

wherein

L= —CH$_2$—, —(CH$_3$)$_2$C—, —(CH$_3$)$_2$C—, —O—, —S—, —SO$_2$— or —CO—;

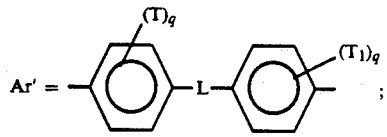

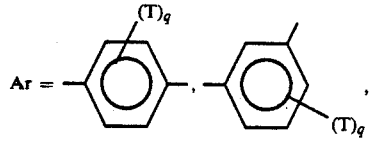

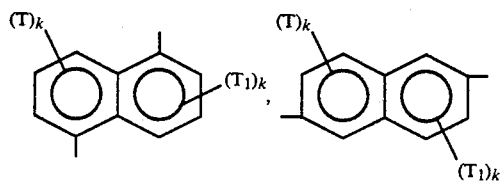

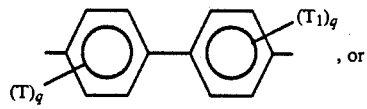

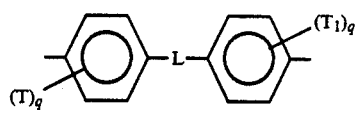

T and T$_1$=lower alkyl, lower alkoxy, aryl, aryloxy, substituted aryl, halogen, or mixtures thereof;
q=0-4;
k=0-3; and
j=0, 1, or 2;
hydroquinone;
bisphenol A;
p,p'-biphenol
4,4'-dihydroxydiphenylsulfide;
4,4'-dihydroxydiphenylether;
4,4'-dihydroxydiphenylisopropane;
4,4'-dihydroxydiphenylhexafluropropane;
a dialcohol having a Schiff base segment, the radical being selected from the group consisting of:

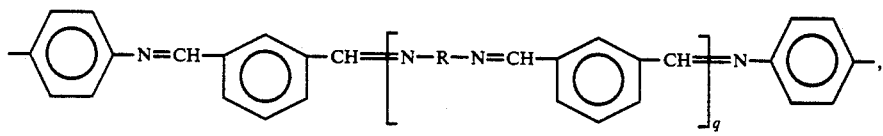

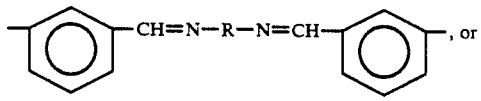

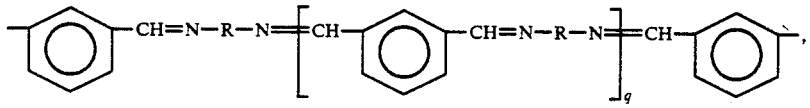

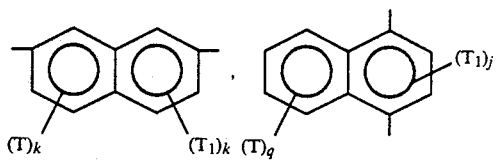

wherein R is selected from the group consisting of: phenyl; biphenyl; naphthyl; or a radical of the general formula:

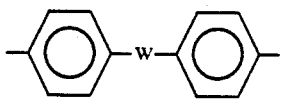

wherein W= —CH$_2$— or —SO$_2$—; or a dialcohol selected from the group:

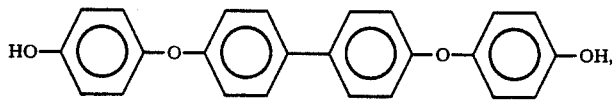

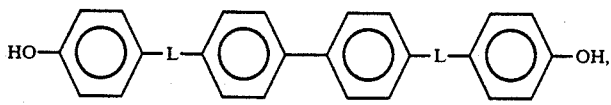

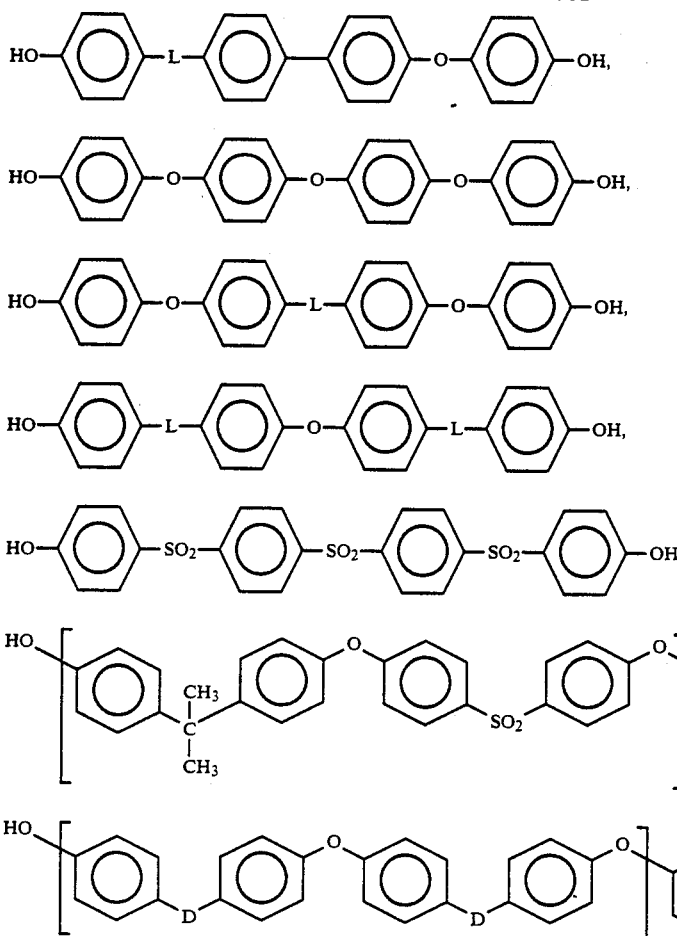

wherein
L is as defined above;
Me=CH₃—;
m=an integer, generally less than 5, and preferably 0 or 1; and
D=any of —CO—, —SO₂—, or —(CF₃)₂C—.

While bisphenol A is preferred (because of cost and availability), the other dialcohols can be used to add rigidity to the oligomer without significantly increasing the average formula weight, and, therefore, can increase the solvent resistance. Random or a block copolymers are possible.

Furthermore, the dialcohols may be selected from the dihydric phenol imide sulfone resins described in U.S. Pat. No. 4,584,364, which is incorporated by reference, or those dihydric phenols described in U.S. Pat. Nos. 3,262,914 or 4,611,048. In fact, the hydroxy-terminated etherimides of U.S. Pat. No. 4,611,048 can be reacted with A—NO₂ to provide crosslinking etherimides of the present invention.

Dialcohols of this nature are commercially available. Some may be easily synthesized by reacting halide intermediates with bis-phenates, such as by the reaction of 4,4'-chlorophenylsulfone with bis(disodium biphenolate).

The oligomers can be synthesized in a homogeneous reaction scheme wherein all the reactants are mixed at one time (and this scheme is preferred), or in a stepwise reaction. The diamine and dialcohols can be mixed, for example, followed by addition of the nitrophthalic anhydride to initiate the polymerization and thereafter the end caps to quench it. Those skilled in the art will recognize the variant methods that might be used. To the extent possible, undesirable competitive reactions should be minimized by controlling the reaction steps (i.e., addition of reactants) and the reaction conditions.

Instead of Schiff base linkages in the dialcohols, these compounds might include oxazole, thiazole, or imidazole linkages. All of these linkages present the potential for creating conductive or semiconductive composites, if suitably doped.

Dopants for creating semiconductive or conductive composites are preferably selected from compounds commonly used to dope other polymers, namely (1) dispersions of alkali metals (for high activity) or (2) strong chemical oxidizers, particularly alkali perchlorates (for lower activity). Arsenic compounds and elemental halogens, while active dopants, are too dangerous for general usage, and are not recommended.

The dopants react with the polymers to form charge transfer complexes. N-type semiconductors result from doping with alkali metal dispersions. P-type semiconductive result from doping with elemental iodine or perchlorates.

While research into conductive or semiconductive polymers has been intense, the resulting compounds (mainly polyacetylenes, polyphenelenes, and polyvinylacetylenes) are unsatisfactory for aerospace applications because the polymers are:
(a) unstable in air;
(b) unstable at high temperatures;
(c) brittle after doping;
(d) toxic because of the dopants; or
(e) intractable.

These problems may be overcome or significantly reduced with the conductive oligomers of the present invention.

While conventional theory holds that semiconductive polymers should have (1) low ionization potentials, (2) long conjugation lengths, and (3) planar backbones, there is an inherent trade-off between conductivity and toughness or processibility, if these constraints are followed. To overcome the processing and toughness shortcomings common with Schiff base, oxazole, imidazole, or thiazole oligomers, the oligomers of the present invention, include "sulfone" linkages interspersed along the backbone providing a mechanical swivel for the rigid, conductive segments of the arms.

Since it is difficult to include the oxazole, imidazole, or thiazole linkages in the reactants, Schiff base compounds are preferred. The principle focus of the invention is toward improved etherimide, thioetherimides, or sulfoneimides, and the conductive or semiconductive composites are not the preferred compounds of the present invention. They are but a small subset of the compounds that comprise the present invention.

Solubility of the oligomers becomes an increasing problem as the length of the backbones increases. Therefore, shorter backbones are preferred, so long as the resulting oligomers remain processible. That is, the backbones should be long enough to keep the oligomers soluble the reaction sequence.

Blends of the crosslinkable oligomers and noncrosslinking, compatible polymers can also be made. These blends generally comprise substantially equimolar mixtures of the oligomer and polymer. The polymer should have a backbone substantially identical with the oligomer, and may be made in accordance with a process described in U.S. Pat. Nos. 4,297,474 or 3,847,869.

Impact resistance of the cured composites formed from prepregs of the oligomers can be increased without deleterious loss of solvent resistance by forming the prepregs with such a blend. Generally, the blend includes capped oligomers to provide crosslinking upon curing and noncrosslinking polymers of a corresponding backbone to provide compatibility of the oligomer and polymer. A 50-50 blend on a molar basis of oligomers and polymer may be formed by (a) dissolving the capped oligomer in a suitable first solvent, (b) dissolving the uncapped polymer in a separate portion of the same solvent or in a solvent miscible with the first solvent, (c) mixing the two solvent solutions to form a lacquer, and (d) applying the lacquer to fabric in a conventional prepregging process.

Although the polymer in the blend usually has the same backbone (structure and formula weight) as the oligomer, the properties of the composite formed from the blend can be adjusted by altering the ratio of formula weight for the polymer and oligomer.

The terminal groups of the polymer are unimportant so long as the polymer's terminal groups do not react with or impede the crosslinking of the oligomer end caps. Also, it is probably nonessential that the oligomer and polymer have identical repeating units (structure), but that the oligomer and polymer merely be compatible in the solution prior to sweeping out as a prepreg. Of course, if the polymer and oligomer have identical backbones, compatibility in the blend is more likely.

The noncrosslinking polymer can be made by the same synthetic method as the oligomer with the substitution of a quenching cap for the crosslinking end cap. For example, phenol can replace end caps of the formula A—OH; aniline can replace end caps of the formula A—NH$_2$; and, nitrobenzene can replace end caps of the formula A—NO$_2$.

While the best blends are probably those in which the backbones are essentially identical and of modest formula weight and those in which the oligomer and polymer are in equimolar proportions, other variant blends may be prepared, as will be recognized by those of ordinary skill in the art.

Anhydrides of the formula:

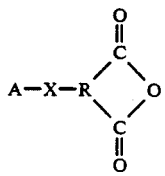

wherein
X=—O— or —S—;
R=a trivalent C$_{(6-13)}$ aromatic organic radical;

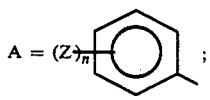

n=1 or 2;

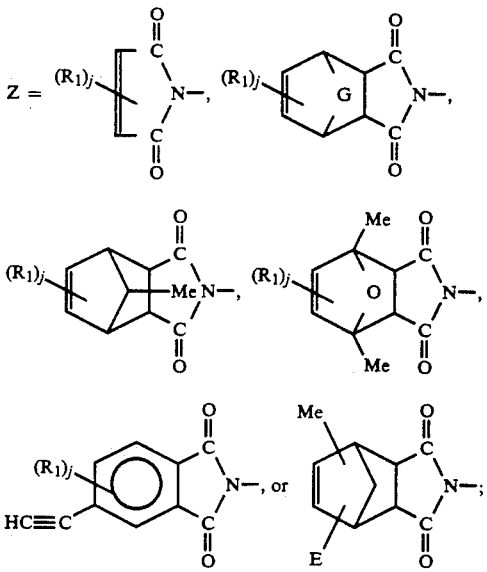

R$_1$=any of lower alkyl, lower alkoxy, aryl, or substituted aryl;
j=0, 1, or 2; and
G=—CH$_2$—, —O—, —S—, or —SO$_2$—,
are useful in the synthesis of the etherimides of the present invention, and are prepared by the condensation of the corresponding end cap phenol or thiol (—XH)

with a nitro- or halo-anhydride that contains the R moiety.

In at least one synthesis of the etherimides of the present invention, a compound of the formula:

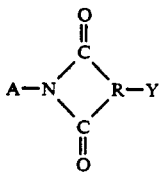

is an intermediate or reactant, wherein:

R=a trivalent $C_{(6-13)}$ aromatic organic radical'

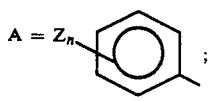

n=1 or 2;

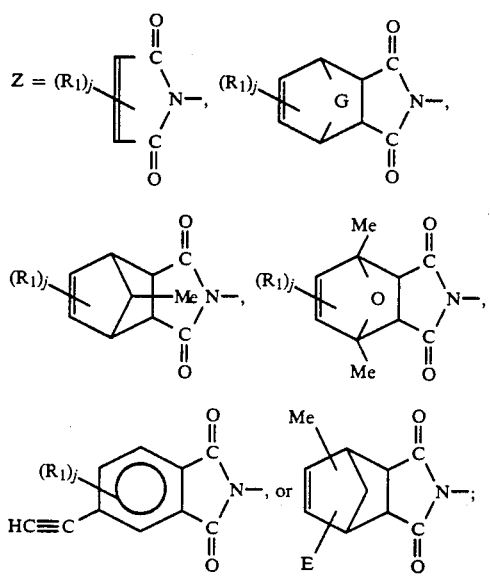

E=allyl or methallyl;
$R_1$=any of lower alkyl, lower alkoxy, aryl, or substituted aryl;
j=0, 1, or 2; and
G=—CH$_2$—, —O—, —S—, or —SO$_2$—

This intermediate if formed by reacting A—NH$_2$ with a substituted phthalic anhydride of the formula:

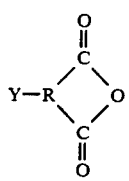

wherein Y=halo- or nitro-. These substituted anhydrides are described in U.S. Pat. Nos. 4,297,474 and 3,847,869.

Polysulfoneimide oligomers can be prepared by reacting about m+1 moles of a dianhydride with about m moles of a diamine and about 2 moles of an amine end cap (A—NH$_2$). The resulting oligomer has the general formula:

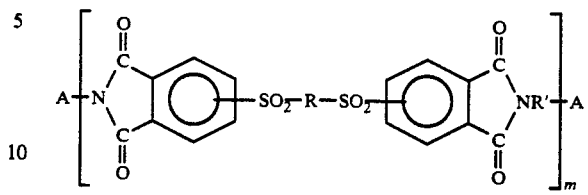

wherein R and R' are divalent aromatic organic radicals having from 2-20 carbon atoms. R and R' may include halogenated aromatic C(6-20) hydrocarbon derivatives; alkylene radicals and cycloalkylene radicals having from 2-20 carbon atoms; $C_{(2-8)}$ alkylene terminated polydiorganosiloxanes; and radicals of the formula:

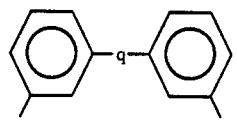

wherein
q=—C$_y$H$_{2y}$—, —CO—, —SO$_2$—, —O—, or —S—; and
y=1 to 5.

Comparable polymers, usable in blends of the sulfoneimides, are described in U.S. Pat. No. 4,107,147, which is incorporated by reference. Other aromatic dithio dianhydrides are described in U.S. Pat. No. 3,933,862.

The oligomers of the present invention can be combined with reinforcing materials, such as fibers, chopped fibers, whiskers, or fabrics, and cured to composite materials using heat or chemicals to activate crosslinking between end caps. Prepregs can be prepared by conventional prepregging techniques. Curing generally is conducted in conventional vacuum bagging techniques at elevated temperatures. The curing temperature varies with the choice of end cap. If desired, mixtures of end caps might be used.

While para-isomerism has generally been described, other isomers may be used. The phenyl or aryl moieties in the backbones can also include substituents so long as the substituents do not interfere with the crosslinking or synthesis. While polyaryl compounds are described, aliphatic moieties can be included in the backbones, in some cases, although the ultimate use temperatures of these oligomers or composites may be lower than with entirely polyaryl backbones.

While preferred embodiments have been described, those skilled in the art will readily recognize alterations, variations, or modifications which might be made to the embodiments without departing from the inventive concept. Therefore, the claims should be interpreted liberally with the support of the full range of equivalents known to those of ordinary skill based upon this description. The claims should be limited only as is necessary in view of the pertinent prior art.

We claim:

1. A method of making polyetherimide oligomers comprising the step of:
    condensing a mixture of about 2m+2 moles of nitrophthalic anhydride of the formula:

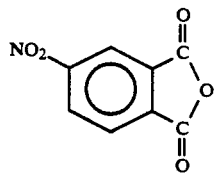

with about m+1 moles of diamine, about m moles of dialcohol, and about 2 moles of A—OH, wherein

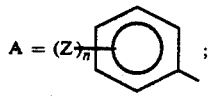

n = 1 or 2;
m = an integer greater than or equal to 1;
E = allyl or methallyl;
R = a trivalent $C_{(6-13)}$ aromatic organic radical;
$R_1$ = any of lower alkyl, lower alkoxy, aryl, or substituted aryl;

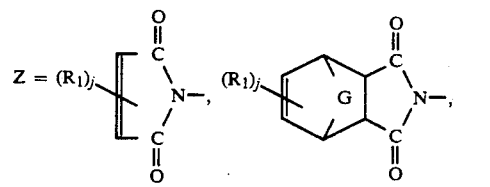

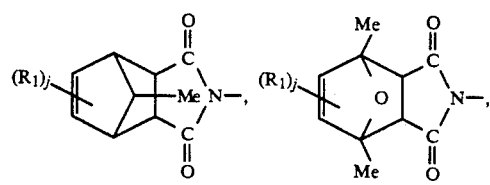

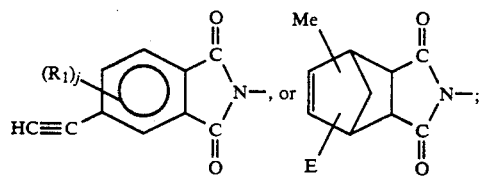

j = 0, 1, or 2; and
G = —$CH_2$—, —O—, —S—, or —$SO_2$—.

2. The polyetherimide oligomer that is the product of the process of claim 1.

3. A method for making polyetherimide oligomers comprising the step of:
condensing about 2m+2 moles of nitrophthalic anhydride with about m+1 moles of dialcohol, about m moles of diamine, and about 2 moles of A—$NH_2$, wherein:

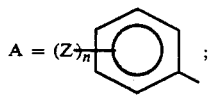

n = 1 or 2;
m = an integer greater than or equal to 1;
E = allyl or methallyl;
$R_1$ = any of lower alkyl, lower alkoxy, aryl, or substituted aryl;

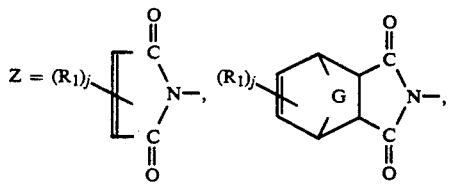

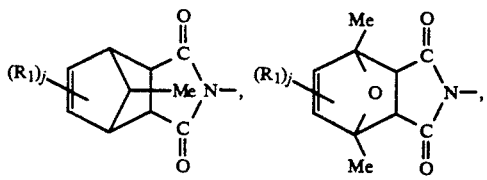

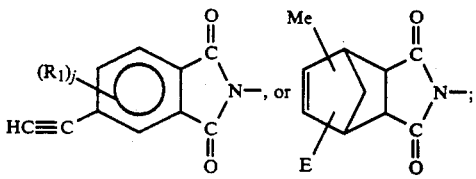

j = 0, 1, or 2; and
G = —$CH_2$—, —O—, —S—, or —$SO_2$—.

4. The polyetherimide oligomer that is the product of the process of claim 3.

5. A method for making polyetherimide oligomers comprising the step of:
condensing about 2m moles of nitrophthalic anhydride with about m+1 moles of dialcohol, about m moles of diamine, and about 2 moles of A—$NO_2$, wherein:

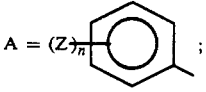

n = 1 or 2;
m = an integer greater than or equal to 1;
E = allyl or methallyl;
$R_1$ = any of lower alkyl, lower alkoxy, aryl, or substituted aryl;

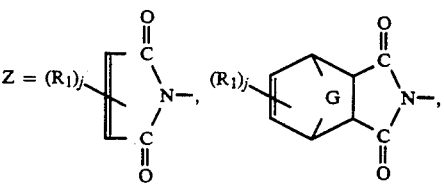

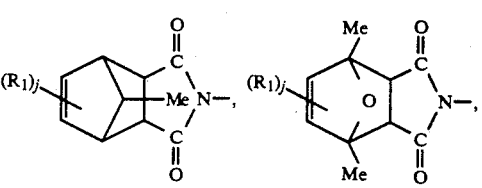

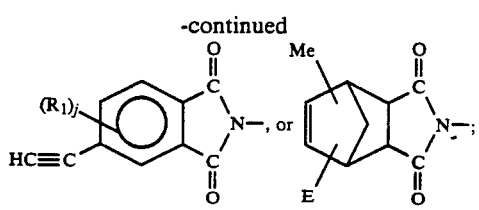

j=0, 1, or 2; and
G=—CH₂—, —O—, —S—, or —SO₂—.

6. The polyetherimide oligomer that is the product of the process of claim 5.

7. A polyetherimide oligomer, comprising the product of the process of reacting a dialcohol and a nitro-terminated end cap, the dialcohol having the formula:

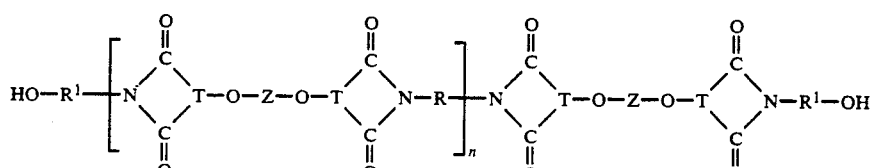

wherein
n is an integer of from about 3 to about 12;
—O—T< is selected from the group consisting of:

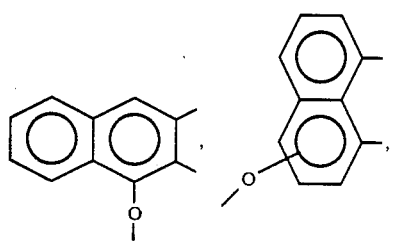

or

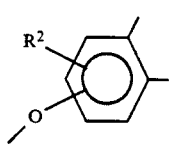

wherein
R² is hydrogen, lower alkyl or lower alkoxy;
Z is a member of the group consisting of:

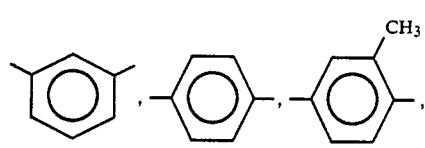

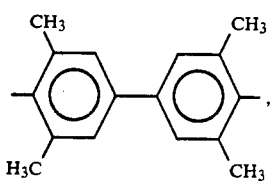

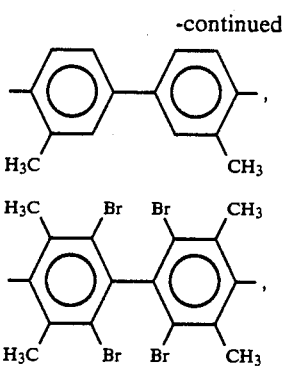

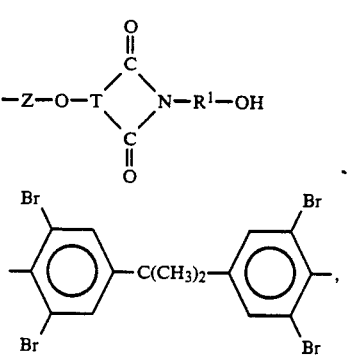

and divalent organic radicals of the general formula:

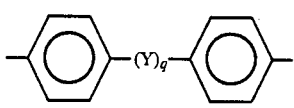

wherein Y is a member selected from the group consisting of divalent radicals of the formula:

—C$_y$H$_{2y}$—, —CO—, —SO₂—, —O—, and —S— where q is 0 or 1, and y is a whole number from 1 to 5; and

R and R₁ are divalent organic radicals independently selected from the group consisting of aromatic hydrocarbon radicals having from 6-20 carbon atoms and halogenated derivatives thereof, alkylene radicals and cycloalkylene radicals having from 2-20 carbon atoms, C$_{(2-8)}$ alkylene terminated polydiorganosiloxane, and divalent radicals included by the formula:

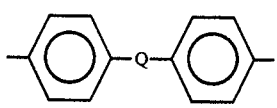

where Q is a member selected from the group consisting of:

—O—, —CO—, —SO₂—, and —C$_x$H$_{2x}$— where x is a whole number from 1 to 5 inclusive; and the nitro-terminated end cap having the formula A—NO$_2$ wherein A is selected from the group consisting of:

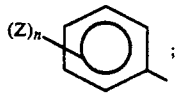

n is 1 or 2;

Z is

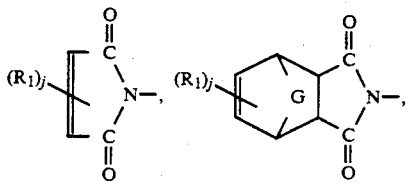

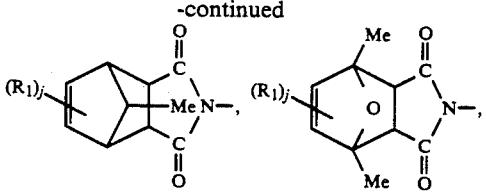

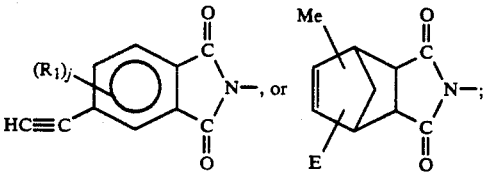

E is allyl or methallyl;
R$_1$ is any of lower alkyl, lower alkoxy, aryl, or substituted aryl;
j is 0, 1, or 2;
G is —CH$_2$—, —O—, —S—, or —SO$_2$—; and
Me is methyl.

8. A blend comprising the oligomer of claim 7 and a compatible polyetherimide polymer.

9. A prepreg comprising the blend of claim 8 and a reinforcing additive in fiber or particulate form.

10. A composite comprising the cured oligomer of claim 7.

11. A composite comprising the cured blend of claim 8.

12. A prepreg comprising the oligomer of claim 7 and a reinforcing additive in fiber or particulate form.

* * * * *